US008190551B2

(12) United States Patent
Busch et al.

(10) Patent No.: US 8,190,551 B2
(45) Date of Patent: May 29, 2012

(54) CLASSIFICATION OF FABRICS BY NEAR-INFRARED SPECTROSCOPY

(75) Inventors: Kenneth W. Busch, Waco, TX (US); Christopher B. Davis, Live Oak, TX (US); Marianna Busch, Waco, TX (US)

(73) Assignee: Baylor University, Waco, TX (US)

( * ) Notice: Subject to any disclaimer, the term of this patent is extended or adjusted under 35 U.S.C. 154(b) by 713 days.

(21) Appl. No.: 12/083,282

(22) PCT Filed: Oct. 11, 2006

(86) PCT No.: PCT/US2006/039702
§ 371 (c)(1),
(2), (4) Date: Apr. 16, 2009

(87) PCT Pub. No.: WO2007/047299
PCT Pub. Date: Apr. 26, 2007

(65) Prior Publication Data
US 2010/0036795 A1      Feb. 11, 2010

Related U.S. Application Data

(60) Provisional application No. 60/726,452, filed on Oct. 13, 2005.

(51) Int. Cl.
*G06F 17/00* (2006.01)
*G06N 7/04* (2006.01)
(52) U.S. Cl. ........................................................ 706/54
(58) Field of Classification Search .................. None
See application file for complete search history.

(56) References Cited

OTHER PUBLICATIONS

Morgan et al. "Forensic Discrimination of Dyed Textile Fibers using UV-VIS and Fluorescence Microspectrophotometry", Proc. of the European Fibres, 2004, pages: 11.*
Candolfi et al. "Identification of pharmaceutical excipients using NIR spectroscopy and SIMCA", Journal of Pharmaceutical and Biomedical Analysis, 19 (1999) pp. 923-935.*
Montalvo "A Comparative Study of NIR Diffuse Reflectance of Cottons Grouped According to Fiber Cross-Sectional Dimensions. Part I: Fundamentals", Applied Spectroscopy, vol. 45, Issue 5, 1991, pp. 779-789.*
Kadolph, Sara J., et al.; "Textile Fibers and Their Properties"; Textiles; vol. 9, Chapter 3, pp. 17-31, 2002.
Soyemi, O., et al.; "Design of a Modular, Dispersive Spectrometer for Fundamental Studies in NIR Spectroscopy"; Spectroscopy, vol. 16, pp. 24-33, Apr. 2001.

* cited by examiner

*Primary Examiner* — Jeffrey A Gaffin
*Assistant Examiner* — Li-Wu Chang
(74) *Attorney, Agent, or Firm* — Jackson Walker L.L.P.

(57) ABSTRACT

A method for classifying textile samples and unknown fabrics into known categories using spectroscopy, chemometric modeling, and soft independent modeling of class analogies ("SIMCA"). The method involves collecting spectral data, preferably diffuse near infrared reflectance data, for a library of known fabric samples, creating a database of principal component analyses for each type of fabric, and using SIMCA to classify an unknown fabric sample according to the database.

6 Claims, 7 Drawing Sheets

CLASSIFICATION OF FABRICS BY NEAR-INFRARED SPECTROSCOPY

This application claims priority to U.S. Provisional Patent Application Ser. No. 60/726,452, entitled "CLASSIFICATION OF FABRICS BY NEAR-INFRARED SPECTROSCOPY" filed on Oct. 13, 2005, having K. Busch, C. Davis, and M. Busch, listed as the inventor(s).

BACKGROUND

This invention pertains to the determination of textile composition through the use of spectroscopy and chemometric modeling.

The identification of textiles is a concern around the world. Textile manufactures, retail marketers, and customs officials would all appreciate and utilize a new, fast, non-destructive method of fabric identification. For manufactures and marketers, this method would assure that the garments that are being made and sold are not made of substandard materials or being sold at over-inflated prices. Traditionally, analytical methods for determining fiber content include simple visual inspection with the naked eye, burn testing, microscopy, and solubility testing. These methods, though proven to be effective, have some drawbacks. Visual inspection, for instance, requires the examiner to have a working knowledge of the textiles he will be analyzing. Also, the feel and appearance of some fibers can be extremely similar to another. Microscopy shares the same drawback as visual inspection. Certain manufacturing processes can change the appearance of a fiber. Fibers viewed under the microscope, especially manufactured fibers, often have similar characteristics making a positive identification impossible. Burn and solubility testing can identify the class of fibers, but the technique is destructive and produces waste. (Kadolph et al., 2002).

SUMMARY

In one aspect, the current method for classifying fabrics involves assembling a library of fabric samples, creating a database of diffuse near-infrared reflection spectra of those fabric samples, and using chemometric techniques to classify the fabrics on the basis of their spectra.

A chemometric technique known as Soft Independent Modeling of Class Analogy ("SIMCA") classification is used in conjunction with the database of spectral data from the fabric samples to sort unknown fabric samples into their appropriate fiber type. No chemical or other pretreatment is necessary. The method works regardless of the fabric color or pattern, or the presence or absence of fabric finishes. The method has the advantage of being non-destructive and the operator does not have to have a background in textiles in order to identify the piece of fabric. Moreover, the instrument will fit on a tabletop and does not require specialized laboratory facilities to operate.

Multivariate regression is widely known in many areas of chemistry and can serve as a particularly powerful computational tool for correlating spectral data with known compositional changes in a test set of samples. The basic objective of the method is to develop a mathematical model that relates two sets of variables to each other so that the independent or X-variables can be used to determine the dependent or Y-variable.

To avoid problems with colinearity in the data, all multivariate regression techniques require an orthogonal basis set or coordinate system on which to represent the data. To achieve this condition, modern regression techniques employ projection methods to obtain a series of variance-scaled eigenvectors that can serve as a new coordinate system for the data. This form of data decomposition assures an orthogonal coordinate system for the data. At the same time, it provides a way to reduce the dimensionality of the data because only the major eigenvectors are needed to represent the data. Finally, when the data are represented on the new coordinate system, new insight is often gained as new relationships that were formerly obscured in the old coordinate system are revealed.

Broadly, one aspect of the present invention involves a method for classifying fabrics, comprising the steps of:

(1) Collecting spectral data of a plurality of fabric samples, wherein the fabric samples are of different known fabric types;

(2) Performing a principal component analysis and regression of the spectral data for each of the fabric samples of each known fabric type to create a database of model principal component analyses for each known fabric type;

(3) Collecting spectral data of an unknown fabric sample to give unknown spectral data; and (4) Using the database of model principal component analyses and soft independent modeling of class analogy ("SIMCA") to classify the unknown fabric sample into either one or more of the different known fabric types or a type of unknown origin.

In the current invention, the preferred spectral data is diffuse near-infrared reflection ("NIR") spectral data. The method is quite general and can apply to a diversity of fabric types, including acetate, acrylic, blends, cotton, linen, mohair, nylon, olefin, polyester, PVC, rayon, silk, and wool.

This method is useful for the rapid identification of unknown fabric samples. It is non-destructive and does not require hazardous chemicals and solvents. Any entities in need of this technology, such as customs officials, could purchase a standardized near infrared spectrometer, the spectral database, and the software for performing the classification. Because spectral databases are instrument specific, they cannot be transferred to other instruments. Subscribers could receive periodic database updates as more samples are added to the library. Although there is no minimum or maximum number of samples to be included in the library, it should be of sufficiently high a number of samples to create accurate models for prediction.

DETAILED DESCRIPTION OF PREFERRED EMBODIMENTS

Figure 1:
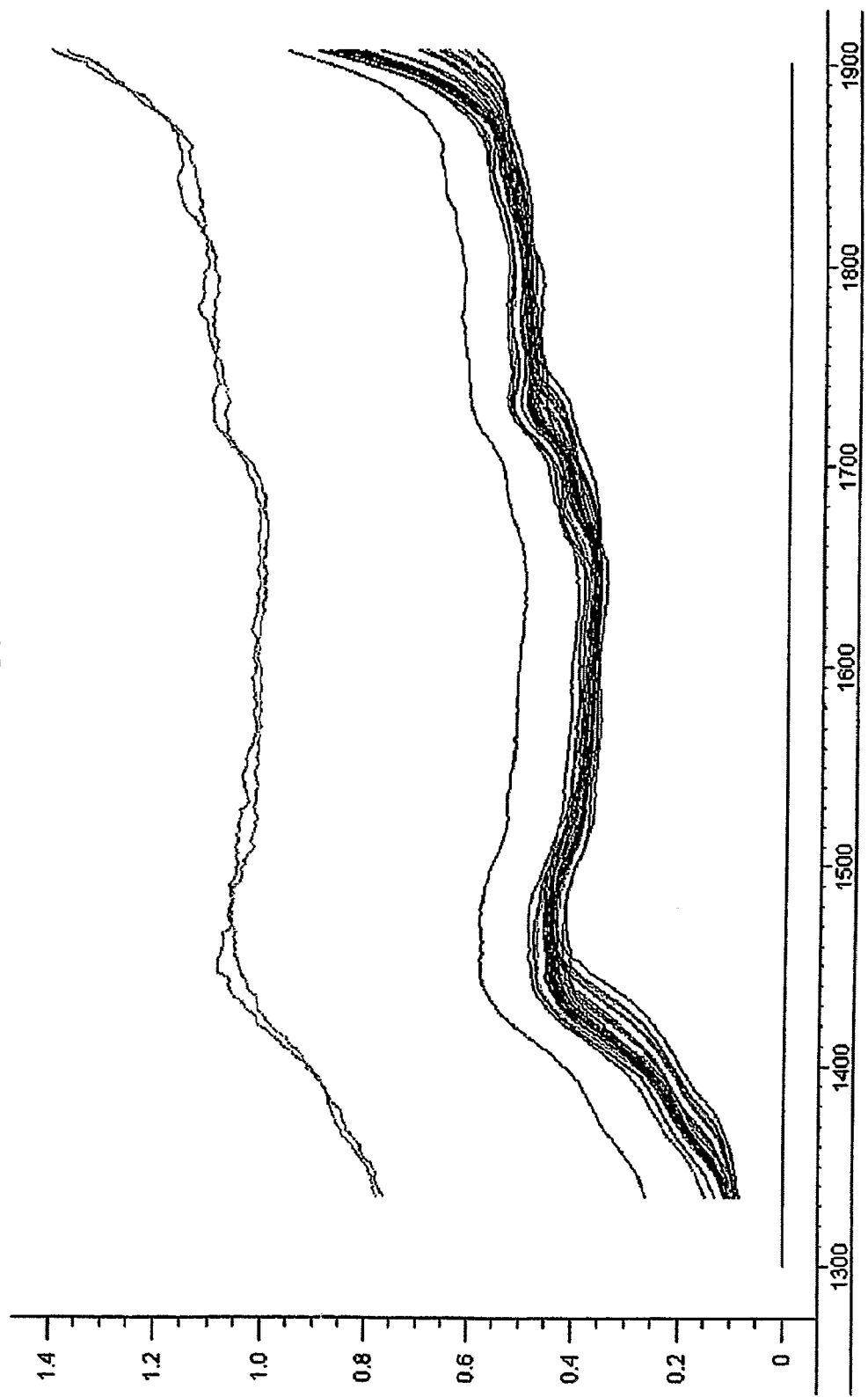
FIG. 1 shows the NIR spectra, (log 1/R) versus wavelength, of acetate samples.
Figure 2:
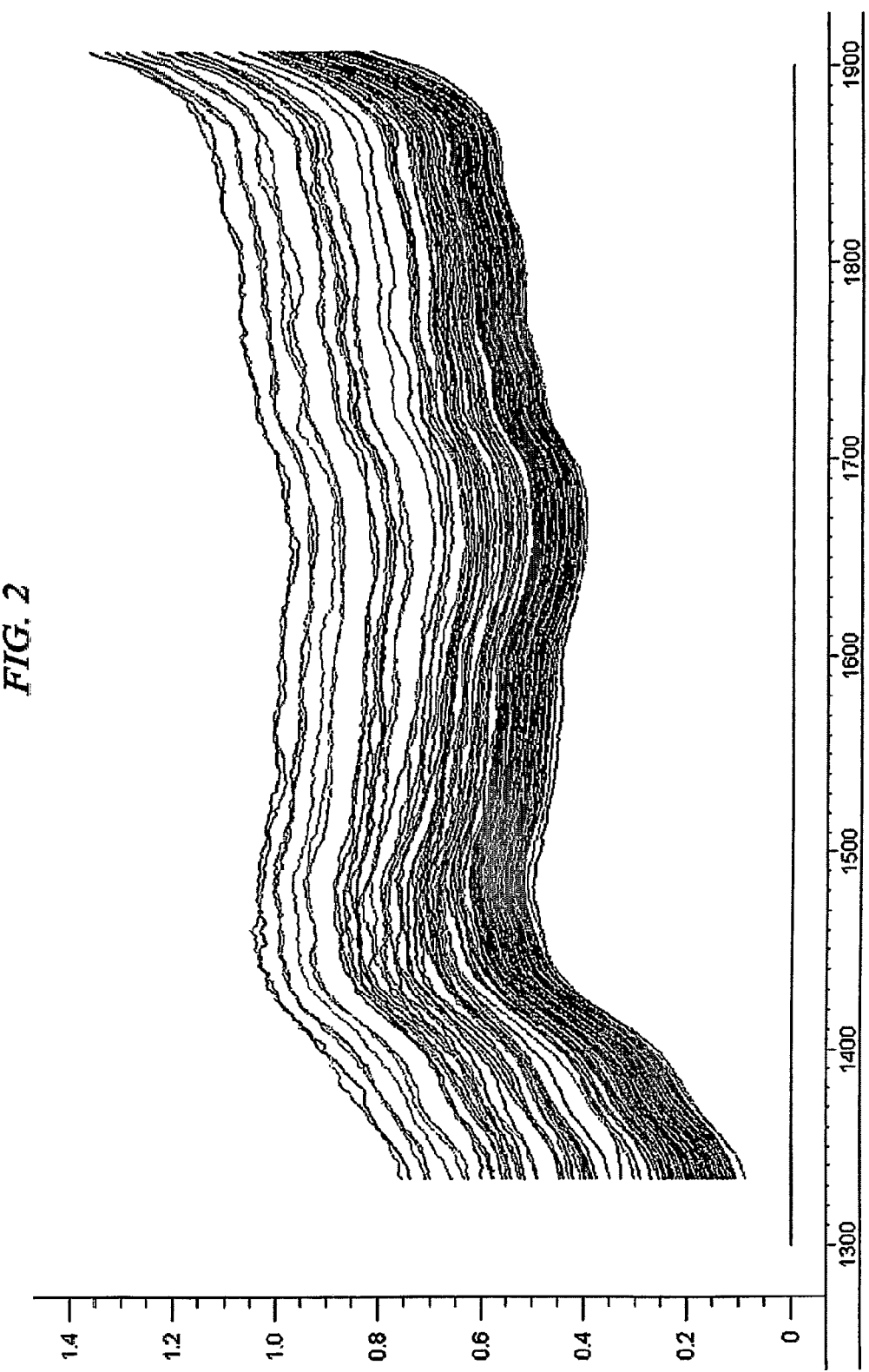
FIG. 2 shows the NIR spectra, (log 1/R) versus wavelength, of cotton samples.
Figure 3:
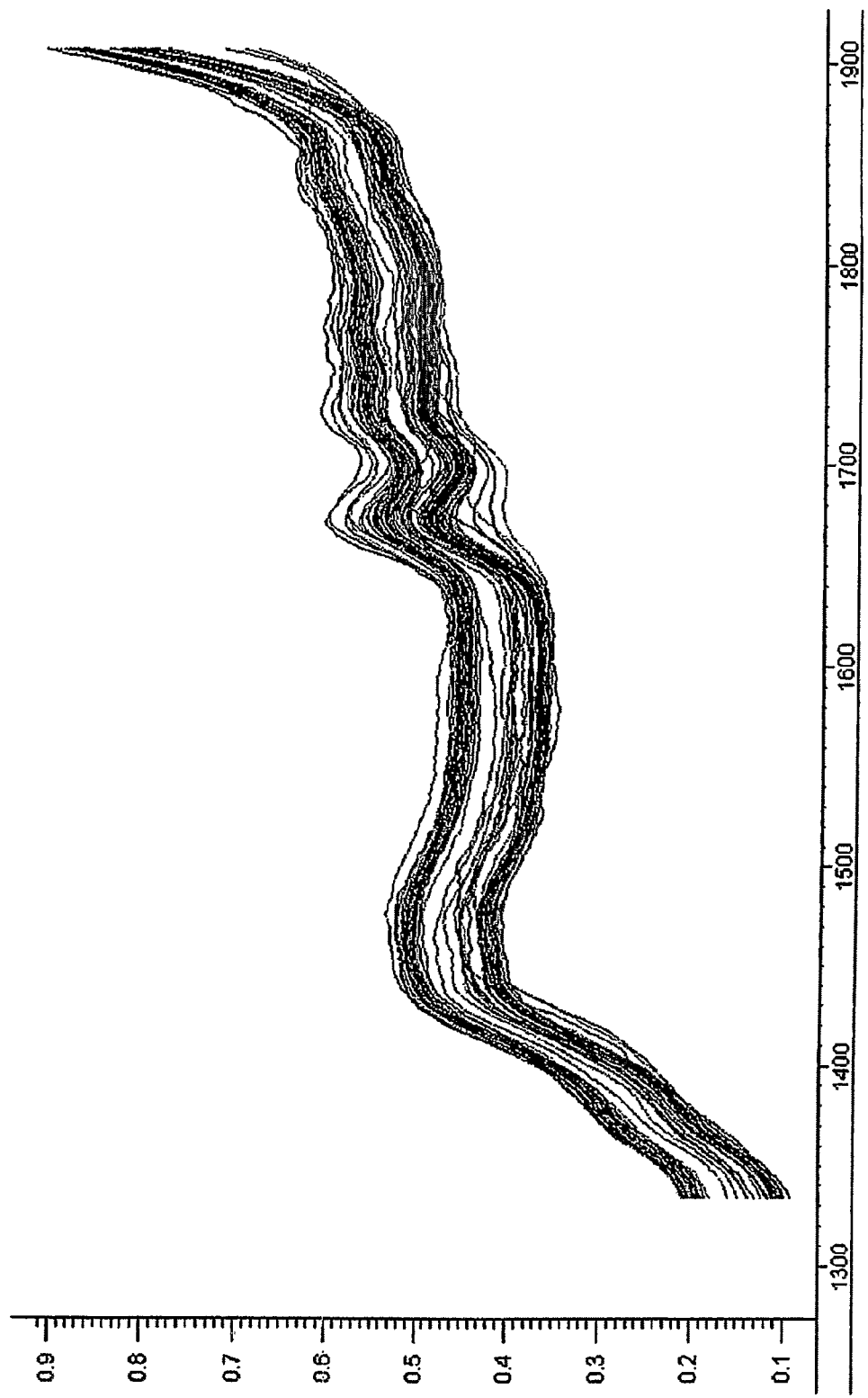
FIG. 3 shows the NIR spectra, (log 1/R) versus wavelength, of polyester samples.
Figure 4:
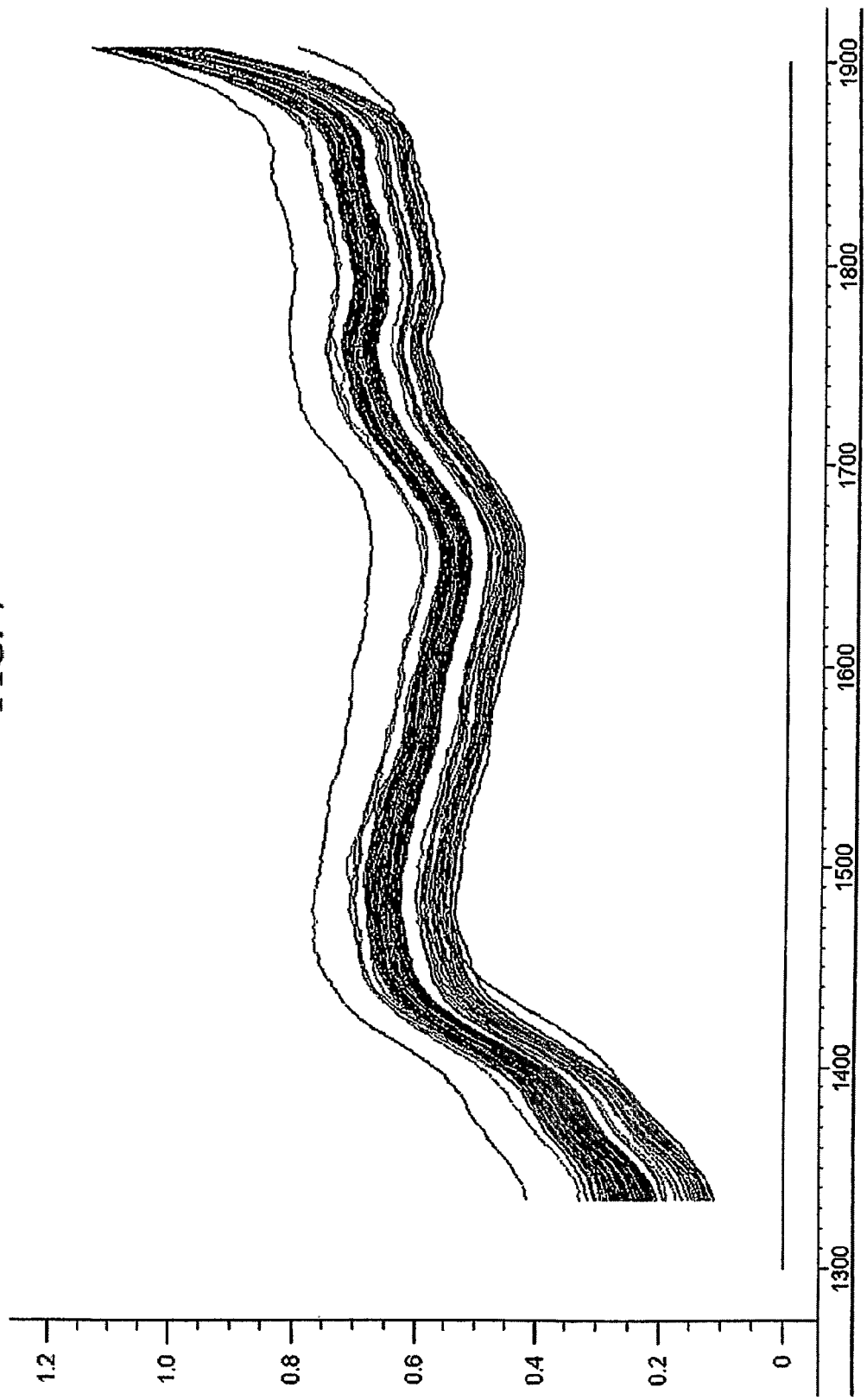
FIG. 4 shows the NIR spectra, (log 1/R) versus wavelength, of wool samples.

The present invention relates to the classification of textiles using spectroscopy and chemometric modeling. In particular, the present invention involves the development of a spectral database of fabric samples and the use of supervised soft independent modeling of class analogies ("SIMCA") to classify unknown fabric samples.

Broadly, the first step in the current method pertains to the development of a database of spectral data of known fabric samples. Preferably, the spectral data collected is diffuse near-infrared reflection ("NIR") spectra. Any suitable spectrometer capable of collecting diffuse NIR spectra can be used. Preferably, the NIR spectrometer includes a quartz halogen source, monochromator, lead sulfide detectors, and an integrating sphere, coated with barium sulphate (Soyemi et al, 2001). Examples of the fabric categories to be sampled for inclusion in the database include acetate, acrylic, blends, cotton, linen, mohair, nylon, olefin, polyester, PVD, rayon, silk, and wool.

The fabric samples should be scanned by the NIR spectrometer in a single layer and should not be folded or crumpled in the sample holder. No sample pretreatment is required. The aperture of the integrating sphere should be fully covered by the fabric sample. After collection of the spectral data for each fabric type, the data is entered into a suitable chemometric analysis program (Unscrambler® 9.1, Camo, Inc., Corvallis, Oreg.). Although no sample pretreatment is required, a Savitzky-Golay smoothing routine is preferably used as a data pretreatment.

The chemometric technique called soft independent modeling of class analogy ("SIMCA") is used in conjunction with the spectral database to sort unknown fabric samples into their appropriate fiber type. SIMCA is a classification method based on disjoint PCA (principal component analysis) modeling. A principal component analysis is done for a given group of samples within a fabric category. This step calibrates the multivariate program so it can discern what sample belongs to which category. In the SIMCA approach, classification in PLS is performed in order to identify local models for possible groups and to predict a probable class membership for new observations. At first, this approach runs a global PCA or PLS regression (according to the available data structure) on the whole dataset in order to identify groups of observations. Local models are then estimated for each class. Finally, new observations are classified to one of the established class models on the basis of their best fit to the respective model.

This approach, enforces the composition of the classes to be the same as the one initially chosen on the basis of the global model, computes the distance of each observation from the model with respect to the explanatory variable, and in order to compute the class membership probabilities, refers to a distribution of this distance whose shape and degrees of freedom, are not yet completely clear and demonstrated.

In SIMCA, a PCA is performed on each class in the data set, and a sufficient number of principal components are retained to account for most of the variation within each class. Hence, a principal component model is used to represent each class in the data set. The number of principal components retained for each class is usually different. Deciding on the number of principal components that should be retained for each class is important, as retention of too few components can distort the signal or information content contained in the model about the class, whereas retention of too many principal components diminishes the signal-to-noise. A procedure called cross-validation ensures that the model size can be determined directly from the data. To perform cross-validation, segments of the data are omitted during the PCA. Using one, two, three, etc., principal components, omitted data are predicted and compared to the actual values. This procedure is repeated until every data element has been kept out once. The principal component model that yields the minimum prediction error for the omitted data is retained. Hence, cross-validation can be used to find the number of principal components necessary to describe the signal in the data while ensuring high signal-to-noise by not including the so-called secondary or noise-laden principal components in the class model. The variance that is explained by the class model is called the modeled variance, which describes the signal, whereas the noise in the data is described by the residual variance or the variance not accounted for by the model.

By comparing the residual variance of an unknown to the average residual variance of those samples that make up the class, it is possible to obtain a direct measure of the similarity of the unknown to the class. This comparison, is also a measure of the goodness of fit of the sample, to a particular principal component model.

When a new unknown sample is introduced, SIMCA will compare the spectral features of the new sample with those principal component analyses the operator wishes to investigate. If the program determines the sample is similar enough to one or more categories, it will classify the sample as such. However, if the sample is considered not to fall into any of the categories defined by the given principal component analyses; it will be rejected and not classified. The SIMCA approach to classification differs from that of partial-least-squares (PLS) discriminant analysis. A discriminant analysis makes the assumption that a new unknown is a member of one of the classes included in the analysis. SIMCA can classify a sample as being in s single group, multiple groups, or not in any of the groups presented. This methodology is advantageous in a situation where the sample in question is of unknown origin, and there is absolutely no information about it available. A PLS discriminant analysis could classify the sample as a member of a class even if it wasn't due to the assumption that the sample must fall into one of the prearranged categories.

The spectral data are preferably governed by log 1/R. The data can be transformed to the Kubelka-Munk ("K-M") function using the computer modeling program. The new set of spectra can then be entered into the principal component analyses for the fabric categories. Either type of analyses can be used, although log 1/R is more accurate for predicting unknown fabric classifications.

In particular, the method for classifying fabrics by near-infrared spectroscopy involves the following steps. First, a database of spectral data from a number of fabric samples of various known fabric types is prepared. To prepare the database, spectral data from a plurality of fabric samples of different known fabric types is collected. Then a principal component analysis and partial-least-squares regression is performed using the spectral data collected for each of the different known fabric types. The database then contains model principal component analyses for each of the known fabric types and can be used to classify an unknown fabric sample. The spectral data of the unknown fabric sample is then collected. Finally, the database of model principal component analyses is used in association with SIMCA to classify the unknown fabric sample into either one or more of the different known fabric types or a type of unknown origin. The SIMCA classification method may classify the unknown sample into more than one fabric type. If the SIMCA classification method does not identify a suitable fabric type into which the unknown fabric sample can be classified, it will not place the sample into any of the known categories.

This strategy is useful for determining the fiber content and textile composition of various unknown fabrics, including acetate, acrylic, blends, cotton, linen, mohair, nylon, olefin, polyester, PVC, rayon, silk, and wool. Preferably, the spectral data collected is diffuse near-infrared reflection spectral data.

Example 1

Development of Spectral Database of Fabric Samples

Fabric samples were gathered from sample cards, swatch catalogs, and clippings from actual garments and fabric bolts. In all, a total of 826 samples were collected and placed into the fabric NIR database. A breakdown of the individual fabric categories, and the number of fabric samples in those categories can be seen in Table 1 below.

TABLE 1

Fabric database summary

| Fabric | Samples$^a$,$_{Tot}$ | Samples$^b$,$_{PCA}$ | Samples$^c$,$_{Pred}$ |
|---|---|---|---|
| Acetate | 61 | 51 | 10 |
| Acrylic | 4 | — | — |
| Blends | 50 | — | — |
| Cotton | 274 | 263 | 11 |
| Linen | 5 | — | — |
| Mohair | 2 | — | — |
| Nylon | 4 | — | — |
| Olefin | 1 | — | — |
| Polyester | 109 | 99 | 10 |
| PVC | 1 | — | — |
| Rayon | 77 | 67 | 10 |
| Silk | 46 | 36 | 10 |
| Wool | 192 | 182 | 10 |

($^a$total samples in database; $^b$samples included in PCA; $^c$samples predicted)

The NIR spectrometer used had a quartz halogen source, monochromator, lead sulfide detectors, and an integrating sphere, coated with barium sulphate, which allowed diffuse reflectance measurements to be collected (Soyemi et al., 2001). The NIR spectrometer was attached to and controlled by a personal computer running Labview™ software. No sample pretreatment was preformed. The fabrics were scanned as a single layer and not folded or crumpled in the sample holder. The aperture of the integrating sphere was fully covered by the fabric sample. Each sample was scanned from 1100 to 2200 nm at every 2 nm.

The spectral data for each fabric group were combined into one large spectral data file in the Unscrambler® 9.1 (Camo, Inc., Corvallis, Oreg.) chemometric analysis program. Although there was no sample pretreatment, a Savitzky-Golay smoothing routine was used as a data pretreatment. The wavelength region smoothed was from 1324-1916 nm with five averaging side points on either end of the data.

The wavelength region used in the principal component analyses was from 1334-1906 nm, and each PCA was preformed using full cross validation. For each PCA, six principal components were used in the calculation. Some of the fabric groups such as cotton and polyester could manage with four. However, acetate and wool did not have as much spectral variance explained in their first four PC's.

Figure 5:
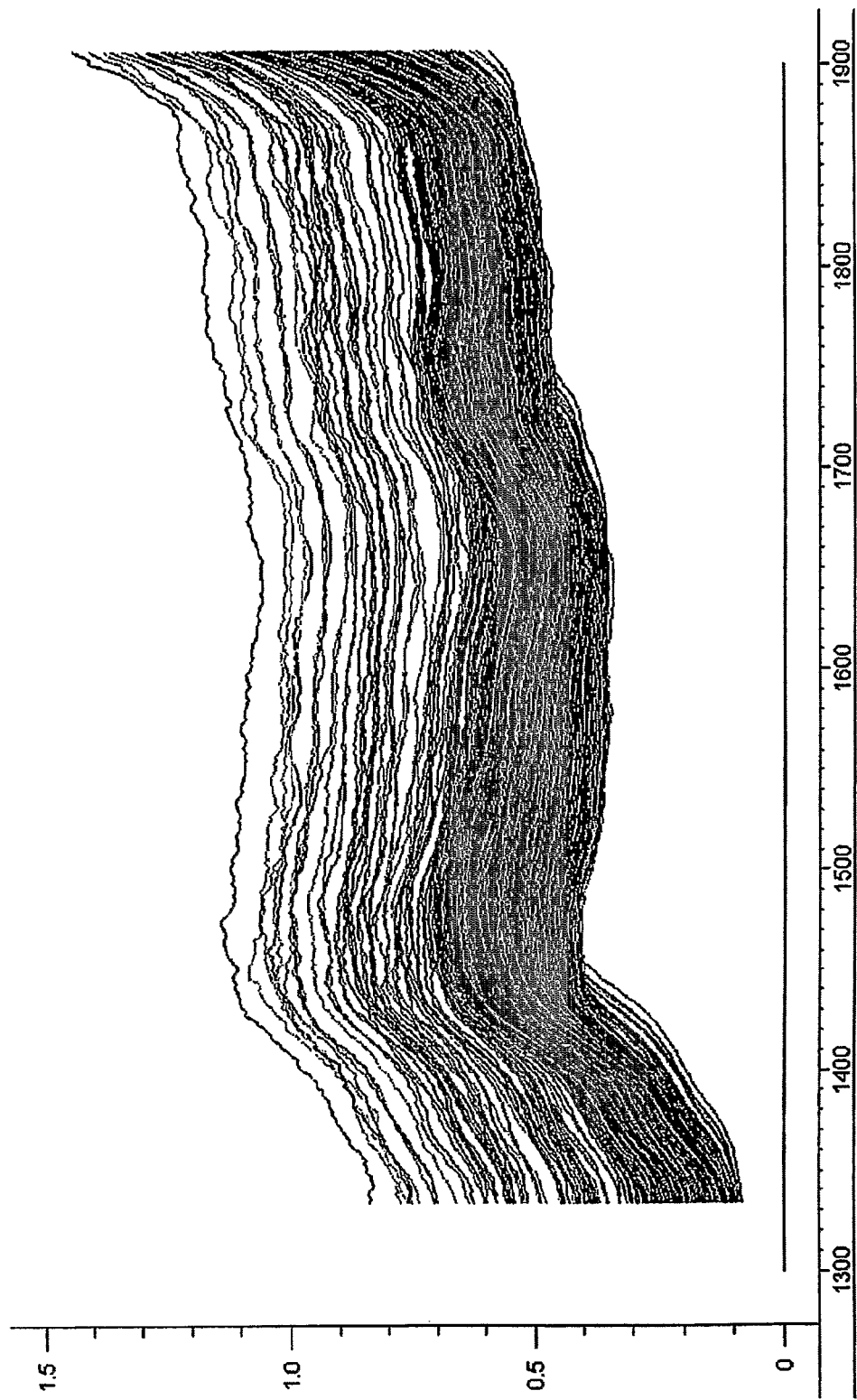
FIG. 5 shows the NIR spectra, (log 1/R) versus wavelength, of all samples in the fabric database.
Figure 6:
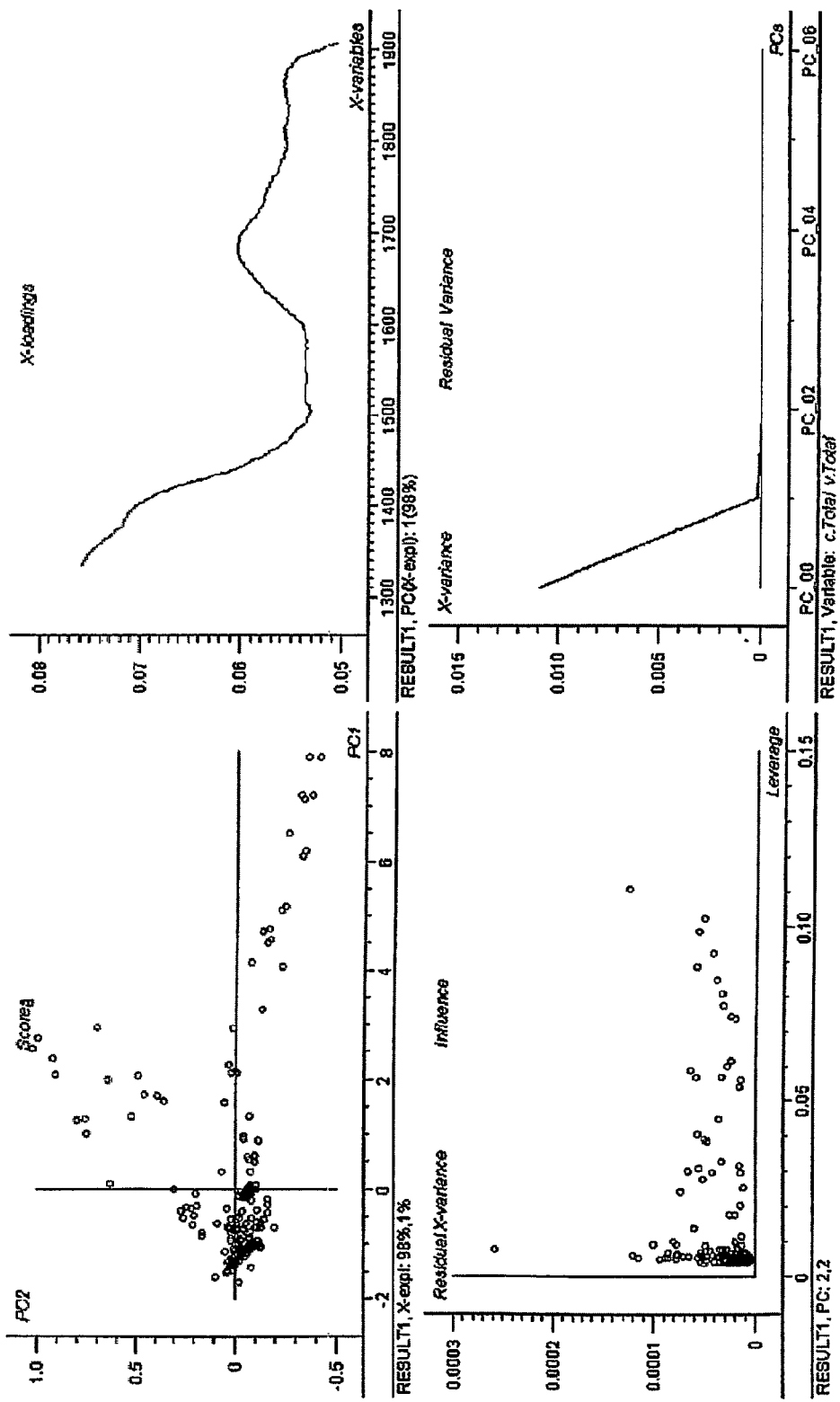
FIG. 6 shows the principal component analysis for the cotton samples: (A) Scores plot; (B) Regression coefficients plot; (C) Residuals plot; and (D) Residual variance plot.
Figure 7:
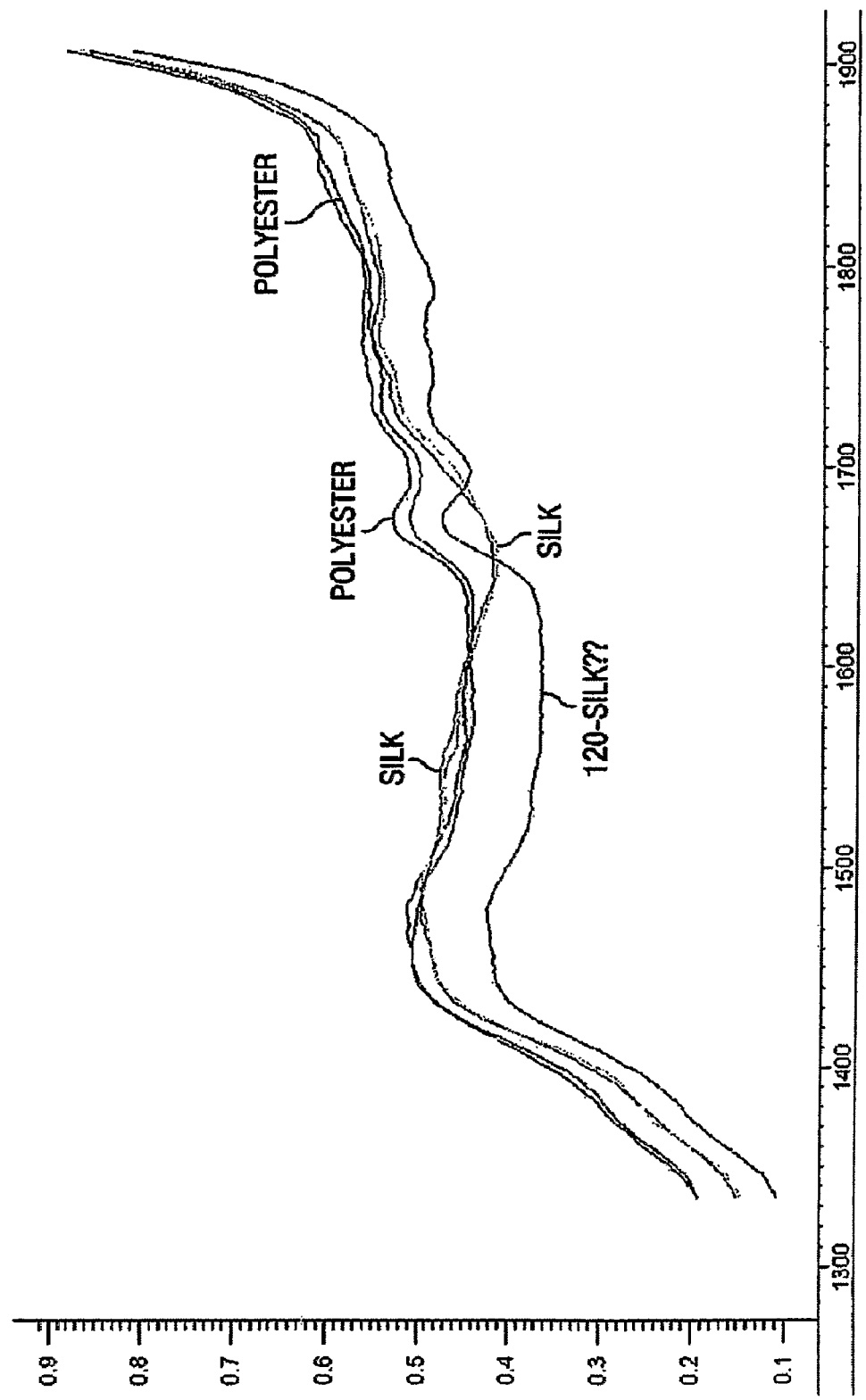
FIG. 7 shows the spectra of representative polyester and silk samples, as well as a sample falsely identified as being silk.

Examples of group spectra for acetate, cotton, polyester, and wool can be seen in FIGS. 1 through 4. FIG. 5 shows the spectra of all 826 samples in the textile database. An example principal component analysis ("PCA") for the cotton fabric samples is shown in FIG. 6.

Example 2

Classification of Unknown Fabric Samples

The model PCA's for acetate, cotton, and wool were used to classify a set of unknowns. The unknowns consisted of 10 acetate, polyester, and wool, as well as 11 cotton samples. The result of this analysis can be seen in Table 2 below. All of the samples were classified in the appropriate category with no additional misclassifications.

TABLE 2

| Sample | Acetate log 1-R | Cotton log 1-R | Polyester log 1-R | Wool log 1-R |
|---|---|---|---|---|
| 1-Acetate | * | | | |
| 516-Acetate | * | | | |
| 581-Acetate | * | | | |
| 585-Acetate | * | | | |
| 595-Acetate | * | | | |
| 596-Acetate | * | | | |
| 597-Acetate | * | | | |
| 612-Acetate | * | | | |
| 614-Acetate | * | | | |
| 615-Acetate | * | | | |
| 22-Cotton | | * | | |
| 23-Cotton | | * | | |
| 34-Cotton | | * | | |
| 104-Cotton | | * | | |
| 105-Cotton | | * | | |
| 634-Cotton | | * | | |
| 635-Cotton | | * | | |
| 671-Cotton | | * | | |
| 672-Cotton | | * | | |
| 849-Cotton | | * | | |
| 850-Cotton | | * | | |
| 52-Polyester | | | * | |
| 56-Polyester | | | * | |
| 59-Polyester | | | * | |
| 74-Polyester | | | * | |
| 75-Polyester | | | * | |
| 534-Polyester | | | * | |
| 535-Polyester | | | * | |
| 557-Polyester | | | * | |
| 558-Polyester | | | * | |
| 570-Polyester | | | * | |
| 324-Wool | | | | * |
| 366-Wool | | | | * |
| 389-Wool | | | | * |
| 406-Wool | | | | * |
| 416-Wool | | | | * |
| 426-Wool | | | | * |
| 440-Wool | | | | * |
| 447-Wool | | | | * |
| 459-Wool | | | | * |
| 504-Wool | | | | * |

The spectra in this study were generated by log 1/R. The reflectance data could be converted to the Kubelka-Munk (K-M) function; however, the conversion showed no improvement in the classification analysis.

Example 3

Classification of Mislabeled Sample

By coincidence, it was found that one of the fabric samples in the database created in Example 1 was apparently mislabeled. A specific silk sample was repeatedly not classified as a silk when compared to the silk PCA. Under the assumption that the silk sample may not be a silk, it was screened against all the models that had been produced for this study. The sample did not get a positive classification until it was compared to the polyester PCA, as shown in Table 4 below.

TABLE 4

| Sample | Polyester log 1-R |
|---|---|
| 13-Silk | |
| 24-Silk | |
| 37-Silk | |
| 39-Silk | |
| 40-Silk | |
| 42-Silk | |
| 43-Silk | |
| 44-Silk | |
| 58-Silk | |
| 67-Silk | |
| 68-Silk | |
| 69-Silk | |
| 70-Silk | |
| 76-Silk | |
| 77-Silk | |
| 78-Silk | |
| 80-Silk | |
| 81-Silk | |
| 84-Silk | |
| 92-Silk | |
| 98-Silk Satin | |
| 99-Silk Satin | |
| 108-Silk | |
| 109-Silk | |
| 117-Silk | |
| 118-Silk | |
| 119-Silk | |
| 120-Silk | * |
| 994-Silk | |
| 995-Silk | |
| 996-Silk | |
| 997-Silk | |
| 998-Silk | |
| 999-Silk | |
| 1000-Silk | |
| 1001-Silk | |
| 1002-Silk | |
| 1003-Silk | |
| 1004-Silk | |
| 1005-Silk | |
| 1006-Silk | |
| 1007-Silk | |
| 1008-Silk | |
| 1009-Silk | |
| 1010-Silk | |
| 1011-Silk | |

This prompted a closer examination of the spectrum of the "fake" silk and the spectra of several silk and polyester samples. The principal NIR band at 1672 nm present in the two accepted polyester samples can clearly be seen in the questionable silk sample, as shown in FIG. 8. This indicates that the sample is in fact a polyester and not a silk. Those wishing to fake a silk garment typically use polyester due to the finishes that are used on the fibers.

REFERENCES CITED

The entire content of each of the following documents is hereby incorporated by reference.

OTHER PUBLICATIONS

Kadolph, et al., *Textile Fibers and Their Properties*, vol. 9, pp. 17-31, 2002
Soyemi, et al., *Spectroscopy*, vol. 16, pp. 24-33, 2001

What is claimed is:

1. A method for classifying unknown fabric samples, comprising:
    providing an unknown fabric sample;
    collecting spectral data of the unknown fabric sample using a near-infrared reflection spectrometer to give a spectrum of an unknown sample;
    collecting near-infrared spectral data of a plurality of fabric samples to create a spectral database for regression analysis, wherein the fabric samples are of known fabric types;
    performing a principal component analysis and a regression of the spectral data for each of the fabric samples of each known fabric type; and
    using soft independent modeling of class analogy ("SIMCA") to compare the spectrum of the unknown sample to similar spectral data of the known standard representing the known fabric type to classify the unknown fabric sample into either one or more of the known fabric types.

2. The method of claim 1, wherein the spectral data is diffuse near-infrared reflection spectral data.

3. The method of claim 1, wherein the known fabric types comprise one or more of acetate, acrylic, blends, cotton, linen, mohair, nylon, olefin, polyester, PVC, rayon, silk, and wool.

4. A method for classifying unknown fabric samples, comprising:
    collecting spectral data of a plurality of fabric samples using a near-infrared spectrometer, wherein the fabric samples are of known fabric types;
    performing a principal component analysis and a regression of the spectral data for each of the fabric samples of each known fabric type to create a database of model principal component analyses for each known fabric type;
    collecting spectral data of an unknown fabric sample using a near-infrared spectrometer to give unknown spectral data; and
    using the database of model principal component analyses and soft independent modeling of class analogy ("SIMCA") to classify the unknown fabric sample into either one or more of the known fabric types or a type of unknown origin.

5. The method of claim 4, wherein the spectral data is diffuse near-infrared reflection spectral data.

6. The method of claim 4, wherein the known fabric types comprise one or more of acetate, acrylic, blends, cotton, linen, mohair, nylon, olefin, polyester, PVC, rayon, silk, and wool.

* * * * *